United States Patent [19]
Shirai et al.

[11] Patent Number: 5,618,708
[45] Date of Patent: Apr. 8, 1997

[54] PROCESS FOR PRODUCTION OF INOSITOL AND MICROORGANISM USED THEREFOR

[75] Inventors: Makoto Shirai, Anjo; Tetsu Yonehara, Nagoya, both of Japan

[73] Assignee: Toray Industries, Inc., Tokyo, Japan

[21] Appl. No.: 425,066

[22] Filed: Apr. 19, 1995

[30] Foreign Application Priority Data

Apr. 19, 1994 [JP] Japan .................................. 6-080064
Jul. 27, 1994 [JP] Japan .................................. 6-175315
Jul. 27, 1994 [JP] Japan .................................. 6-175316

[51] Int. Cl.$^6$ .................................. C12P 7/02; C12N 1/14
[52] U.S. Cl. .................. 435/155; 435/254.22; 435/921
[58] Field of Search .................................. 435/155, 921, 435/254.22

[56] References Cited

U.S. PATENT DOCUMENTS 5,296,364  3/1994  Agrawal ................................. 435/155

FOREIGN PATENT DOCUMENTS 0506289  9/1992  European Pat. Off. .

OTHER PUBLICATIONS

Klig et al.(1990) *J. of Bacteriology*, vol. 172, 8:4407–14.
Klig et al. (1990) *YEAST*, vol. 7:325–336.

*Primary Examiner*—Herbert J. Lilling
*Attorney, Agent, or Firm*—Birch, Stewart, Kolasch & Birch, LLP

[57] ABSTRACT

A process for production of inositol comprising the steps of (1) culturing a microorganism capable of extracellularly secreting inositol and belonging to the genus Candida in a medium so as to extracellularly accumulate inositol in the medium; and optionally (2) recovering inositol from the culture. Preferably, the producer microorganism is resistant to an antibiotic such as cerulenine or D-cycloserine, or resistant to a glucose metabolism antagonist such as 2-deoxyglucose.

19 Claims, No Drawings

PROCESS FOR PRODUCTION OF INOSITOL AND MICROORGANISM USED THEREFOR

BACKGROUND OF INVENTION

1. Field of Invention

The present invention relates to a process for production of inositol and novel producer microorganisms useful for said process.

2. Related Art

As process for the production of inositol, so far, a process wherein inositol is extracted from rice bran or corn steep liquor (E.P. No. 506289, 1992) (Japanese Unexamined Patent Publication No. 61-56142) and a process wherein Baker's yeast (*Saccharomyces cerevisiae*) is cultured and inositol is recovered from the culture (E.P. No. 506289, 1992) are known.

However the extraction method is disadvantageous in that rice bran and corn steep liquor contain a large amount of various impurities, and therefore, purification of inositol from an extract from the rice bran or corn steep liquor is difficult and expensive. On the other hand, in the process wherein Baker's yeast is cultured, productivity is low and therefore this process is also expensive, and an industrial process using Baker's yeast has not yet been developed. So far, microorganisms, other than Baker's yeast, which extracellularly secrete inositol are not known.

SUMMARY OF INVENTION

The present inventors, after various research to find microorganisms, other than Baker's yeast, which can extracellularly secrete inositol, found that a mutant of a microorganism belonging to the genus Candida extracellularly secretes inositol. In addition, the present inventors found that inositol can be produced not only by a conventional fermentation process wherein a producer microorganism is grown in a medium containing carbon source and nitrogen source to extracellularly secrete inositol and the inositol is recovered from the culture, but also by a process wherein a producer microorganism is cultured to obtain cultured cells, and the resting cells, which are not growing, are used in the form of a cultural broth, and separated intact cells or modified cells extracellularly secrete inositol. In the latter process enzyme reactions not accompanied with cell growth participate in the production of inositol.

Accordingly, the present invention provide a process for production of inositol comprising the steps of culturing a microorganism belonging to the genus Candida and capable of extracellularly secreting inositol in a medium to extracellularly accumulate inositol, and optionally recovering the inositol from the culture.

In addition the present invention provide a process for production of inositol comprising the steps of culturing a microorganism belonging to the genus Candida and capable of extracellularly secreting inositol in a medium to obtain cultured cells containing enzymes necessary for the synthesis of inositol, incubating the enzymes with a precursor of inositol so as to convert the precursor to inositol and extracellularly accumulate inositol, and optionally recovering the inositol.

According to a preferred embodiment, the present invention uses, as a producer microorganism, a microorganism capable of extracellularly secreting inositol, belonging to the genus Candida and resistant to an antibiotic.

Therefore, the present invention further provides a process for production of inositol comprising the steps of culturing a microorganism capable of extracellularly secreting inositol, belonging to the genus Candida and resistant to an antibiotic in a medium to extracellularly accumulate inositol, and optionally recovering the inositol from the culture.

The present invention also provide a process for production of inositol comprising the steps of culturing a microorganism capable of extracellularly secreting inositol, belonging to the genus Candida and resistant to an antibiotic in a medium to obtain cultured cells containing enzymes necessary for the synthesis of inositol, incubating the enzymes with a precursor of inositol so as to convert the precursor to inositol and extracellularly secreting the inositol, and optionally recovering the inositol.

According to another embodiment of the present invention, the present invention uses, as a producer microorganism, a microorganism capable of extracellularly secreting inositol, belonging to the genus Candida and resistant to a glucose metabolism antagonist.

Accordingly, the present invention provides a process for production of inositol comprising the steps of culturing a microorganism capable of extracellularly secreting inositol, belonging to the genus Candida and resistant to a glucose metabolism antagonist in a medium to extracellularly accumulate inositol, and optionally recovering the inositol.

The present invention also provides a process for production of inositol comprising the steps of culturing a microorganism capable of extracellularly secreting inositol, belonging to the genus Candida and resistant to a glucose metabolism antagonist in a medium to obtain cultured cells containing enzymes necessary for the synthesis of inositol, incubating the enzymes with a precursor for inositol so as to convert the precursor to inositol and extracellularly accumulate inositol, and optionally recovering the inositol.

According to the present invention, any microorganism belonging to the genus Candida and capable of extracellularly secreting inositol can be used. A preferable microorganism belonging to the genus Candida is *Candida boidinii*. For example, *Candida boidinii* mutant IP-2 derived from *Candida boidinii* TR-1 is preferable. Note, *Candida boidinii* TR-1 was designated TR-1, deposited with National Institute of Bioscience and Human-Technology Agency of Industrial Science and Technology as FERM P-14261 on Apr. 4, 1994, and transferred to an international deposition under the Budapest Treaty as FERM BP-5076 on Apr. 14, 1995; and *Candida boidinii* IP-2 was designated IP-2, deposited with National Institute of Bioscience and Human-Technology Agency of Industrial Science and Technology as FERM P-14262 on Apr. 4, 1994, and transferred to an international deposition under Budapest Treaty as FERM BP-5077 on Apr. 4, 1995.

*Candida boidinii* TR-1 and *Candida boidinii* IP-2 commonly have the following properties.

(a) Cultural and morphological properties (1) Culturing in a malt extract liquid medium Cells abundantly grow and have yellow to cream color, and are homogeneously suspended. A cell is long elliptical and slightly curved. Size of a cell is 1.5–3.5× 7–12 μm.

(2) Culturing on a malt extract solid medium

Colony is of yellow to cream color, clear and smooth, soft, and wettish.

(3) Growing on plate culture of corn meal agar medium

Cells link to form a chain-like a mycelium which sometimes branches.

(b) Spore formation

Spores are not formed on some media including a malt extract agar medium.

(c) Physiological and Chemotaxonomical properties

| | |
|---|---|
| (1) Optimum growth conditions pH 3 to 7; temperature 15 to 37° C. | |
| (2) Tolerable conditions pH 2 to 9; temperature 4 to 47° C. | |
| (3) Death temperature 50° C. | |
| (4) Nitrate assimilation | positive |
| (5) Gelatin liquefying | negative |
| (6) Growth on ethanol as sole carbon source | abundant |
| (7) Carotenoid production | positive |
| (8) Lythmus milk reaction | negative |
| (9) Ester production | negative |
| (10) Fatty acid splitting | negative |
| (11) Acid production | positive |
| (12) Production of starch-like substance | negative |
| (13) Diazonium Blue B reaction | negative |
| (14) Fermentation of sugars: | Glucose, |

(14) Fermentation of sugars: Glucose, galactose and mannose well fermented; starch, threharose and arabinose very slightly fermented; galactose, maltose, saccharose, rhaffinose and inositol not fermented.

(15) Assimilation of sugar: Glucose, fructose, lactose, mannose, xylose and mannitol highly assimilated; galactose slightly or not assimilated; saccharose, maltose, rhaffinose arabinose, dextrin, starch, inuline, arabinose, rhaffinose and inositol not assimilated.

(16) Utilization of carbon sources: Methanol, ethanol and glycerol well utilized; pyruvate, fumarate, α-ketoglutarate and isopropanol utilized; citrate, propanol, ethylene glycol, propylene glycol, acetaldehyde, glycine, glutamate, aspartate and L-alanine slightly utilized.

(17) Utilization of nitrogen source:

Peptone, ammonium sulfate, ammonium nitrate, sodium nitrate, urea, thiourea, L-glutamate, glycine, DL-alanine and asparagine utilized; sodium nitrite not utilized.

(18) Requirement of vitamins: biotin is required.

(19) Requirement of amino acids no

Accordingly, the microbial strains TR-1 and IP-2 were identified as *Candida boidinii* in accordance with J. Gen. Appl. Microbial. 26, 133–158 (1980) (especially page 156).

*Candida boidinii* IP-2 representative of the present strains capable of extracellularly secreting inositol is a mutant of a wild strain *Candida boidinii* TR-1. The mutation can be carried out according to a conventional procedure. For example, mutants can be obtained by treating a parent strain such as a wild strain with a physical mutagen such as ultraviolet radiation, or a chemical mutagen such as N-methyl-N'-nitro-N-nitrosoguanidine, ethylmethanesulfonate et al. After the treatment of the parent cells with a mutagen the treated cells can be highly efficiently screened to obtain mutants capable of extracellularly secreting inositol, for example, as follows.

Namely, the treated cells are plated on an agar medium on which the cells can grow well, such as a natural nutrient agar medium so as to form colonies. On the other hand, another agar medium which does not contain inositol and on which the mutated cells such as *Candida boidinii* cells can grow is coated with a cell suspension of an inositol-requiring strain. Next, the colonies generated as described above are replicated on the agar medium as prepared above. If a colony replicated on the agar medium produces inositol and extracellularly secretes the inositol, a few days after, the cells of the inositol-requiring strain previously plated on the agar medium grow around the colony which extracellularly secreted inositol (positive colony). Therefore, a mutant strain extracellularly secreting inositol can be isolated and purified from the original colony corresponding to that positive colony.

Although the ratio of generating desired strain is $1/10^4$ to $1/10^6$, a desired strain can be selected very easily and efficiently according to the above-mentioned screening system. Therefore, although the specification describes the mutant strain TR-1 as a representative of a desired strain, a person with ordinary skill in the art can easily obtain mutants extracellularly secreting inositol once one is taught that the above-mentioned screening system is effective for obtaining the desired strains.

A mutant resistant to an antibody according to the present invention is that which exhibits an antibody resistance higher than the parent strain thereof. Preferably, an antibody resistant mutant of the present invention is that which exhibits at least 60% of relative growth (cell concentration) in a medium containing an antibiotic in which a parent strain exhibits 30% or lower of relative growth (cell concentration). In this case, "relative growth" means the percentage of growth (cell concentration) of a microorganism in a medium containing an antibiotic, taking the growth (cell concentration) of the same microorganism in the same medium but not containing the antibiotic as 100%, wherein the growth (cell concentration) is determined by measuring absorbance at 660 nm.

As antibodies used in the present invention, for example, cerulenine, Brefeldin A, D-cycloserine, and other commercially available antibiotics can be used.

A mutant of the present invention, which can extracellularly secrete inositol, belongs to the genus Candida and is resistant to an antibiotic can be prepared by mutating cells of any strain capable of extracellularly secreting inositol. An example of preferable parent strains to be mutated is *Candida boidinii* IP-2 (FERM BP-5077). The mutation can be carried out according to the procedure described above. To select mutants resistant to an antibiotic, the cells treated with a mutagen are plated on an agar medium containing the antibiotic. In this case, only mutants which have acquired the resistance against the antibiotic can grow and form a colony. Therefore, a desired mutant can be easily selected, again even though the ratio of generating a desired mutation is about $1/10^4$ to $1/10^6$.

As an example of the microorganisms capable of extracellularly secreting inositol and resistant to cerulenin, *Candida boidinii* CER 176 which is a mutant of *Candida boidinii* IP-2 can be mentioned. The mutant *Candida boidinii* CER 176 was designated CER 176, deposited with National Institute of Bioscience and Human-Technology Agency of Industrial Science and Technology as FERM P-14318 on May 20, 1994, and transferred to an international deposition under the Budapest Treaty as FERM BP-5069 on Apr. 6, 1995.

As examples of the microorganisms capable of extracellularly secreting inositol and resistant to D-cycloserine, *Candida boidinii* DCSR 0.2-59 and *Candida boidinii* DCSR 0.3-11 both of which are mutants of *Candida boidinii* IP-2 can be mentioned. The mutant *Candida boidinii* DCSR 0.2-59 was designated DCSR 0.2-59, deposited with National Institute of Bioscience and Human-Technology Agency of Industrial Science and Technology as an international deposition under the Budapest Treaty on Apr. 6, 1995 as FERM BP-5071. The mutant *Candida boidinii* DCSR 0.3-11 was designated DCSR 0.3-11, deposited with National Institute of Bioscience and Human-Technology Agency of Industrial Science and Technology as an international deposition under the Budapest Treaty on Apr. 6, 1995 as FERM BP-5072.

In another preferred embodiment, the present invention uses a glucose metabolism antagonist-resistant mutant, which belongs to the genus Candida and is capable of extracellularly secreting inositol. The glucose metabolism antagonist is (1) a substance which inhibits the growth of a microorganism wherein the inhibition is recovered by the addition of glucose, and (2) a substance which represses or inhibits enzymes involving in biosynthesis of inositol from glucose wherein said repression or inhibition is recovered by the addition of inositol and/or a substance downstream of inositol in inositol metabolism.

The glucose metabolism antagonists include glucose analogues such as 2-deoxyglucose, 1-thioglucose, 5-thioglucose etc.

A mutant of the present invention, which can extracellularly secrete inositol, belongs to the genus Candida and is resistant to a glucose metabolism antagonist can be prepared by mutating cells of any strain capable of extracellularly secreting inositol. An example of a preferred parent strain to be mutated is *Candida boidinii* IP-2 (FERM BP-5077). The mutation can be carried out according to the procedure described above. The cells treated with a mutagen are subjected to a screening procedure to select glucose metabolism antagonist-resistant mutants wherein the mutagen-treated cells are plated on an agar medium containing a glucose metabolism antagonist. The medium for screening must not contain glucose, and contains an alcohol such as glycerol, methanol, ethanol etc. In this case only mutants which have acquired the resistance against glucose metabolism antagonist can grow and form colonies. Therefore, a desired mutant can be easily selected, again even though the ratio of generating a desired mutation is about $1/10^4$ to $1/10^6$.

An example of the glucose metabolism antagonist-resistant strains of the present invention is *Candida boidinii* DGR 1-14, which was designated DGR 1-14, and deposited with National Institute of Bioscience and Human-Technology Agency of Industrial Science and Technology as FERM P-14319 on May 20, 1994, and transferred to an international deposition under the Budapest Treaty on Apr. 6, 1995 as FERM BP-5070.

According to the present invention, inositol is produced by culturing a microorganism capable of extracellularly secreting inositol as described above in a medium containing a carbon source, a nitrogen sources and inorganic ions and if necessary organic trace components to extracellularly accumulate inositol, and if necessary recovering the inositol from the culture (herein called fermentation method).

Alternatively, according to another embodiment of the present invention, inositol is produced by culturing a microorganism capable of extracellularly secreting inositol as described above in a medium in which the microorganism can grow such as the above-mentioned medium to prepare microbial cells containing enzymes participating in the biosynthesis of inositol, and incubating the enzymes with a precursor for biosynthesis of inositol to convert the precursor to inositol, and if necessary recovering the inositol from the reaction medium (herein called enzymatic method).

For the production of inositol by the fermentation method, as a carbon source, for example, sugars such as glucose, fructose, hydrolysate of starch or cellulose, molasses, etc.; an organic acid such as fumaric acid, citric acid, succinic acid etc.; an alcohol such as methanol, ethanol, glycerol etc., alone or in combination, can be used in a fermentation method. The concentration of carbon source is preferably 1 to 15% according to the nature of the carbon source.

As a nitrogen source, for example, organic ammonium salt such as ammonium acetate etc.; inorganic ammonium salt such as ammonium sulfate, ammonium chloride, ammonium phosphate etc.; ammonia such as gaseous ammonia or aqueous ammonia; urea or the like, alone or in combination can be used. The concentration of a nitrogen source is preferably 0.1 to 4.0% according to the nature of the nitrogen source.

As an organic trace component, biotin or other vitamins needed by the microorganism, alone or in combination can be contained in a fermentation medium. The concentration of the organic trace component is preferably 0.000001% to 0.1% according to the nature of the organic trace component. If necessary a material abundantly containing vitamins, amino acids, and other growth factors, for example, corn steep liquor, peptons, yeast extract etc. can be contained in a medium. The concentration of such a material is preferably 0.01 to 5% according to the nature of the material.

In addition, a fermentation medium may contain an inorganic salt such as potassium phosphate, magnesium sulfate, calcium chloride, sodium chloride, zinc sulfate, cupric sulfate, ferrous sulfate, and other trace elements, alone or in combination. The concentration of an inorganic salt is preferably 0.0001 to 0.5% according to the nature of the inorganic material to be added. In addition, if necessary, an antifoam agent may be added to stabilize culturing conditions.

Culturing is preferably carried out under an aerobic condition provided by aeration, agitation and/or shaking. During culturing, the pH value is controlled between 3 and 8, and the culture temperature is controlled between 20° C. and 35° C. Culturing is carried out for 24 to 96 hours, preferably with aeration and agitation.

For the enzymatic method for production of inositol, the cells containing the enzymes participating in the biosynthesis of inositol can be obtained by culturing a microorganism of the present invention in a medium as described above for the fermentation method under the conditions as described for the fermentation method.

Enzymes used in the enzymatic method are preferably used in the form of a culture medium, intact cells separated from the culture medium, protoplast cells prepared by a conventual procedure, disrupted cells in which the enzyme system for biosynthesis of inositol is maintained, or the like.

As a precursor for biosynthesis of inositol, for example, glucose-6-phosphate, or glucose which is a precursor of glucose-6-phosphate etc. can be used. The reaction is preferably carried out in the presence of nicotinamide adenine dinucleotide (NAD) and ammonium ion. Where glucose is used as a precursor, magnesium ion and adenosine-3-phosphate are preferably further added. Those compounds necessary for the synthesis of inositol can be added to a reaction medium separately, or in a form of an organic material containing these compounds. In addition, other substances such as an SH group protecting agent may be added to the reaction medium. The reaction for the synthesis of inositol is preferably carried out at a pH value of 3 to 8, and at a temperature of 20° to 35° C., for 10 to 72 hours, preferably under an aerobic condition provided by aeration and/or agitation.

Inositol accumulated in a culture medium or a reaction medium can be used, for example, as a component of feeds etc. Alternatively, inositol may be isolated and purified from a culture medium or a reaction medium. For example, inositol is isolated and purified according to a procedure conventionally used for isolation or purification of inositol, preferably by centrifuging or filtering a culture medium or a reaction medium to obtain a supernatant or filtrate containing inositol. Next, the supernatant on a filtrate is subjected to cation and anion exchange treatments to eliminate ionic substances, followed by concentration resulting in crystallization of inositol.

EXAMPLES

The present invention is further explained by Examples in more detail.

Example 1

Isolation of Inositol-secreting Mutant

Cells of *Candida boinidii* TR-1 were treated with 300 μg/ml N-methyl-N'-nitro-N-nitrosoguanidine at 30° C. and at pH 6.0 for 10 minutes according to a conventional procedure, appropriately diluted, and plated on an agar medium having a composition shown in Table 1, and the plated cells were cultured at 30° C. for two days.

TABLE 1

| Glucose | 20 g/L |
|---|---|
| Yeast extract | 2 g/L |
| $MgSO_4 \cdot 7H_2O$ | 0.5 g/L |
| Peptone | 5 g/L |
| $K_2HPO_4$ | 1 g/L |

(For agar plate, 15 g/L agar was added.)

On the other hand, cells of *Saccharomyces cerevisiae* ATCC 34893 were inoculated into 5 ml of a medium having a composition shown in Table 1, and cultured at 30° C. for a day with shaking. The cultured cells were washed with physiological saline and plated on an agar plate medium shown in Table 2.

TABLE 2

| Glucose | 10 g/L |
|---|---|
| $(NH_4)_2SO_4$ | 5 g/L |
| $KH_2PO_4$ | 1 g/L |
| $MgSO_4 \cdot 7H_2O$ | 0.5 g/L |
| $CaCl_2 \cdot 2H_2O$ | 0.1 g/L |
| NaCl | 0.1 g/L |
| $ZnSO_4 \cdot 7H_2O$ | 0.4 mg/L |
| $FeSO_4 \cdot 7H_2O$ | 0.4 mg/L |
| $CuSO_4 \cdot 5H_2O$ | 0.04 mg/L |
| Biotin | 0.04 mg/L |
| Agar | 15 g/L | pH 5.5 with 1N KOH

Next, colonies of the mutagen-treated *Candida boidinii* TR-1 formed on the above-mentioned agar plate having the composition shown in Table 1 were replicated on the above-prepared agar plate medium having the composition shown in Table 1, on which cells of *Saccharomyces cerevisiae* had been coated. The replicated colonies around which cells of *Saccharomyces cerevisiae* ATCC 34893 grew were selected as positive colonies, and mutants were isolated and purified from the colonies on the original agar plate corresponding to the replicated positive colonies. In this way, a desired mutant, *Candida boidinii* IP-2 was obtained.

Example 2

Production of Inositol by Fermentation

*Candida boidinii* TR-1 as a control and *Candida boidinii* IP-2 of the present invention were separately precultured in a medium having a composition shown in Table 3, at 30° C. for 24 hours with shaking, and the resulting preculture was inoculated into 50 ml of a medium having the composition shown in Table 3 in a 500 ml conical flask, which had been sterilized at 110° C. for 10 minutes. The cells were cultured for 48 hours with shaking with 30 cm reciprocating span at 180 rpm.

TABLE 3

| Glucose | 50 g/L |
|---|---|
| $(NH_4)_2SO_4$ | 2.5 g/L |
| $KH_2PO_4$ | 1 g/L |
| $MgSO_4 \cdot 7H_2O$ | 0.5 g/L |
| $CaCl_2 \cdot 2H_2O$ | 0.1 g/L |
| NaCl | 0.1 g/L |
| $ZnSO_4 \cdot 7H_2O$ | 0.4 g/L |
| $FeSO_4 \cdot 7H_2O$ | 0.4 g/L |
| $CuSO_4 \cdot 5H_2O$ | 0.04 g/L |
| Biotin | 0.04 g/L | pH 5.5 with 1N KOH

After culturing, the cultured cells and remaining calcium carbonate were eliminated, and an inositol concentration of the supernatant was measured by bioassay following the method of DIFCO Manual (10th Ed., pages 1092–1095 (1984). As a result, the control strain *Candida boidinii* TR-1 did not extracellularly accumulate a detectable amount of inositol (0 g/L), while the mutant of the present invention, *Candida boidinii* IP-2 extracellularly accumulated 1.5 g/L of inositol.

Example 3

Production of Inositol by Enzymatic Method

The control strain *Candida boidinii* TR-1, and the mutant of the present invention *Candida boidinii* IP-2 were separately cultured in a medium having the composition shown in Table 1 at 30° C. for 24 hours with shaking, and the resulting culture was inoculated into 10 ml of media having the composition shown in Tables 4 and 5 in test tubes having a diameter of 25 mm. The cells were cultured at 30° C. for 24 hours with shaking.

TABLE 4

| Glucose | 10 g/L |
|---|---|
| $(NH_4)_2SO_4$ | 0.5 g/L |
| $KH_2PO_4$ | 2.5 g/L |
| $K_2HPO_4$ | 1 g/L |
| $NH_4Cl_2$ | 4 g/L |

TABLE 5

| Methanol | 2% (V/V) |
|---|---|
| $(NH_4)_2SO_4$ | 2.5 g/L |
| $KH_2PO_4$ | 0.5 g/L |
| $K_2HPO_4$ | 1 g/L |
| $MgSO_4 \cdot 7H_2O$ | 0.5 g/L |
| $NH_4Cl_2$ | 4 g/L |

The cultured cells were separated from the medium by centrifugation, and the separated yeast cells were dispersed in distilled water to a concentration of cells of 80 g/L (dry weight equivalent), and the suspension was allowed to stand at 37° C. for 45 minutes. After that, 4 mol/L D-sorbitol aqueous solution was added to the cell suspension to make a final D-sorbitol concentration 1.5 mol/L, and the whole was allowed to stand at 37° C. for 10 minutes.

The treated cells were suspended in media having the compositions shown in Tables 6 and 7, and the suspensions were incubated at 30° C. for 20 hours with shaking.

TABLE 6

| 100 mm | Tris-HCl buffer (pH 7.5) |
|---|---|
| 14 mM | $NH_4Cl$ |
| 2.7 mM | $MgCl_2.6H_2O$ |
| 0.8 mM | Nicotinamide adenine dinucleotide (NAD) |
| 5 mM | Glucose-6-phosphate (substrate) |

TABLE 7

| 100 mM | Tris-HCl buffer (pH 7.5) |
|---|---|
| 14 mM | $MgCl_2.6H_2O$ |
| 0.8 mM | NAD |
| 5 mM | Glucose (substrate) |
| 2.5 mM | Adenosine-triphosphate |

After the reaction, the reaction medium was filtrated to eliminate the cells, and an inositol concentration in the filtrate was quantitated by bioassay. Result is shown in Tables 8 and 9.

TABLE 8

Substrate: glucose-6-phosphate

| | Inositol concentration (g/L) | |
|---|---|---|
| Strains | Methanol culture | Glucose culture |
| Candida boidinii TR-1 (control) | 0 | 0 |
| Candida boidinii IP-2 (present invention) | 0.3 | 0.5 |

TABLE 9

Substrate: glucose

| | Inositol concentration (g/L) | |
|---|---|---|
| Strains | Methanol culture | Glucose culture |
| Candida boidinii TR-1 (control) | 0 | 0 |
| Candida boidinii IP-2 (present invention) | 0.3 | 0.5 |

Example 4

Purification and Crystallization of Inositol

A supernatant of one liter of the culture obtained in Example 2 was passed through cation exchange resin Diaion SK1B, and flow-through fractions were pooled. The collected flow-through fraction was passed through anion exchange resin Diaion PA316, and flow-through fractions were pooled. This fraction was concentrated to crystallize inositol. In this way, 1 g of crystals of inositol in 97% purity was obtained.

Example 5

Isolation of Cerulenine-resistant Mutant

Cells of Candida boidinii IP-2 were treated with 300 μg/ml of N-methyl-N'-nitro-N-nitrosoguanidine at 30° C. and at pH 6.0 for 10 minutes, and the mutagen-treated cells were appropriately diluted, and coated on a plate medium having the composition shown in Table 10 to which 15 g/L of agar and 40 mg/L of cerulenine were added. The plate was incubated at 30° C. for 4 days, and colonies of mutated Candida boidinii IP-2 formed on the plate were isolated and purified. In this way Candida boidinii CER 176 was obtained.

TABLE 10

| Glycerol | 10 g/L |
|---|---|
| $(NH_4)_2SO_4$ | 5 g/L |
| $KH_2PO_4$ | 1 g/L |
| $MgSO_4.7H_2O$ | 0.5 g/L |
| $CaCl_2.2H_2O$ | 0.1 g/L |
| NaCl | 0.1 g/L |
| $ZnSO_4.7H_2O$ | 0.4 mg/L |
| $FeSO_4.7H_2O$ | 0.4 mg/L |
| $CuSO_4.5H_2O$ | 0.04 mg/L |
| Biotin | 0.04 mg/L | pH 5.5 with 1N KOH

Example 6

Resistance Level of Cerulenine-resistant Mutant

A control strain Candida boidinii IP-2, and a cerulenine-resistant mutant Candida boidinii CER 176 were separately cultured in a medium having the composition shown in Table 11, and the grown cells were collected and washed with physiological saline.

TABLE 11

| Glucose | 20 g/L |
|---|---|
| Yeast extract | 2 g/L |
| $MgSO_4.7H_2O$ | 0.5 g/L |
| Polypeptone | 5 g/L |
| $K_2HPO_4$ | 1 g/L |

The cell suspension thus prepared was inoculated into 5 ml of media having the composition shown in Table 10 and containing 0, 10, 20, 40, and 100 mg/L of cerulenine respectively. After culturing for 72 hours, the growth of cells was measured. The result is shown in Table 12.

TABLE 12

| | Relative growth (%) Concentration of cerulenine added (mg/L) | | | | |
|---|---|---|---|---|---|
| Strain | 0 | 10 | 20 | 40 | 100 |
| IP-2 (control) | 100 | 3.8 | 2.4 | 1.1 | 0.2 |
| CER 176 (present invention) | 100 | 90 | 82 | 67 | 11 |

As seen from the above result, the growth of the cerulenine-resistant mutant of the present invention is not inhibited by high concentration of cerulenine in comparison with the parent strain, revealing that the mutant acquired high cerulenine resistance.

Example 7

Production of Inositol by Fermentation Using Cerulenine-resistant Mutant

A control strain *Candida boidinii* IP-2, and a cerulenine-resistant mutant of the present invention *Candida boidinii* CER 176 were separately precultured in a medium having the composition shown in Table 13 at 30° C. for 24 hours with shaking, and the resulting preculture was inoculated into 50 ml of medium shown in Table 13 in a 50 ml conical flask, which previously had been sterilized at 110° C. for 10 minutes, and culturing was carried out with shaking with 30 cm reciprocating span at 180 rpm for 48 hours.

TABLE 13

| | |
|---|---|
| Glucose | 50 g/L |
| $(NH_4)_2SO_4$ | 2.5 g/L |
| $KH_2PO_4$ | 1 g/L |
| $MgSO_4.7H_2O$ | 0.5 g/L |
| $CaCl_2.2H_2O$ | 0.1 g/L |
| NaCl | 0.1 g/L |
| $ZnSO_4.7H_2O$ | 0.4 g/L |
| $FeSO_4.7H_2O$ | 0.4 mg/L |
| $CuSO_4.5H_2O$ | 0.04 mg/L |
| Biotin | 0.04 mg/L | pH 5.5 with 1N KOH

After culturing, the culture medium was filtrated to eliminate the cells and remaining calcium carbonate, and an inositol concentration in the filtrate was determined by bioassay. As a result, the control strain *Candida boidinii* IP-2 extracellularly accumulated 1.5 g/L of inositol, while the cerulenine-resistant strain of the present invention *Candida boidinii* CER 176 extracellularly accumulated 2.7 g/L of inositol.

Example 8

Production of Inositol By Enzymatic Method Using Cerulenine-resistant Mutant A control strain *Candida boidinii* IP-2, and a cerulenine-resistant mutant of the present invention *Candida boidinii* CER 176 were separately precultured in a medium having the composition shown in Table 11 at 30° C. for 24 hours with shaking, and the resulting preculture was inoculated into 10 ml of media having the compositions shown in Tables 14 and 15 in test tubes having 25 mm diameter, which previously had been sterilized at 115° C. for 10 minutes, and culturing was carried out at 30° C. for 24 hours with shaking.

TABLE 14

| | |
|---|---|
| Glucose | 10 g/L |
| $(NH_4)_2SO_4$ | 2.5 g/L |
| $KH_2PO_4$ | 0.5 g/L |
| $K_2HPO_4$ | 1 g/L |
| $MgSO_4.7H_2O$ | 0.5 g/L |
| $NH_4Cl$ | 4 g/L |

TABLE 15

| | |
|---|---|
| Methanol | 2% (V/V) |
| $(NH_4)_2SO_4$ | 2.5 g/L |
| $KH_2PO_4$ | 0.5 g/L |
| $K_2HPO_4$ | 1 g/L |
| $MgSO_4.7H_2O$ | 0.5 g/L |
| $NH_4Cl$ | 4 g/L |

The cultured cells were separated from the medium by centrifugation and the separated yeast cells were dispersed in distilled water to a concentration of cells of 80 g/L (dry weight equivalent), and the suspension was allowed to stand at 37° C. for 45 minutes. After that, 4 mol/L D-sorbitol aqueous solution was added to the cell suspension to make final D-sorbitol concentration 1.5 mol/L, and the whole was allowed to stand at 37° C. for 10 minutes.

The treated cells were suspended in media having the composition shown in Tables 16 and 17, and the suspension was incubated at 30° C. for 20 hours with shaking.

TABLE 16

| | |
|---|---|
| 100 mM | Tris-HCl buffer (pH 7.5) |
| 14 mM | $NH_4Cl$ |
| 2.7 mM | $MgCl_2.6H_2O$ |
| 0.8 mM | Nicotinamide adenine dinucleotide (NAD) |
| 5 mM | Glucose-6-phosphate (substrate) |

TABLE 17

| | |
|---|---|
| 100 mM | Tris-HCl buffer (pH 7.5) |
| 14 mM | $NH_4Cl$ |
| 2.7 mM | $MgCl_2.6H_2O$ |
| 0.8 mM | NAD |
| 5 mM | Glucose (substrate) |
| 2.5 mM | Adenosine-triphosphate |

After the reaction, the reaction medium was filtrated to eliminate the cells, and an inositol concentration in the filtrate was quantitated by bioassay. Result is shown in Tables 18 and 19.

TABLE 18

Substrate: glucose-6-phosphate

| | Inositol concentration (g/L) | |
|---|---|---|
| Strains | Methanol culture | Glucose culture |
| *Candida boidinii* IP-2 (control) | 0.3 | 0.5 |
| *Candida boidinii* CER 176 (present invention) | 0.6 | 1.0 |

TABLE 19

Substrate: glucose

| | Inositol concentration (g/L) | |
|---|---|---|
| Strains | Methanol culture | Glucose culture |
| *Candida boidinii* IP-2 (control) | 0.3 | 0.5 |
| *Candida boidinii* CER 176 (present invention) | 0.6 | 1.0 |

As seen from the above, the cerulenine-resistant mutant of the present invention shows remarkably enhanced productivity of inositol in comparison with the parent strain.

Example 9

Purification and Crystallization of Inositol

A supernatant of one liter of the culture obtained in Example 7 was passed through cation exchange resin Diaion SK1B, and flow-through fractions were pooled. The collected flow-through fraction was passed through anion exchange resin Diaion PA316, and flow-through fractions were pooled. This fraction was concentrated to crystallize inositol. In this way, 2g of crystals of inositol in 97% purity was obtained.

Example 10

Isolation of 2-Deoxyglucose-resistant Mutant

Cells of *Candida boidinii* IP-2 were treated with 300 μg/ml of N-methyl-N'-nitro-N-nitrosoguanidine at 30° C. and pH 6.0 for 10 minutes, and the mutagen-treated cells were appropriately diluted, and coated on a plate medium having the composition shown in Table 20 to which 15 g/L of agar and 2-deoxyglucose (final concentration 1 mM) were added. The plate was incubated at 30° C. for 4 days, and colonies of mutated *Candida boidinii* IP-2 formed on the plate were isolated and purified. In this way *Candida boidinii* DGR 1-14 was obtained.

TABLE 20

| | |
|---|---|
| Glycerol | 10 g/L |
| $(NH_4)_2SO_4$ | 5 g/L |
| $KH_2PO_4$ | 1 g/L |
| $MgSO_4.7H_2O$ | 0.5 g/L |
| $CaCl_2.2H_2O$ | 0.1 g/L |
| NaCl | 0.1 g/L |
| $ZnSO_4.7H_2O$ | 0.4 mg/L |
| $FeSO_4.7H_2O$ | 0.4 mg/L |
| $CuSO_4.5H_2O$ | 0.04 mg/L |
| Biotin | 0.04 mg/L |
| pH 5.5 with 1N KOH | |

Example 11

Resistant Level of 2-deoxyglucose-resistant Mutant

A control strain *Candida boidinii* IP-2, and a 2-deoxyglucose-resistant mutant *Candida boidinii* DGR 1-14 were separately cultured in a medium having the composition shown in Table 22, and the grown cells were collected and washed with physiological saline.

TABLE 21

| | |
|---|---|
| Glucose | 20 g/L |
| Yeast extract | 2 g/L |
| $MgSO_4.7H_2O$ | 0.5 g/L |
| Polypeptone | 5 g/L |
| $K_2HPO_4$ | 1 g/L |

The cell suspension thus prepared was inoculated into 5 ml of media having the composition shown in Table 20 and containing 0, 0.25, 0.5, 0.75, and 1.0 mM 2-deoxyglucose respectively. After culturing for 72 hours, the growth of cells was measured. The result is shown in Table 22.

TABLE 22

| | Relative growth (%) Concentration of 2-deoxyglucose added (mM) | | | | |
|---|---|---|---|---|---|
| Strain | 0 | 0.25 | 0.5 | 0.75 | 1.0 |
| IP-2 (control) | 100 | 26 | 2 | 1 | 1 |
| DGR 1-14 (present invention) | 100 | 94 | 94 | 77 | 53 |

As seen from the above result, the growth of 2-deoxyglucose-resistant mutant of the present invention is not inhibited by high concentration of 2-deoxyglucose in comparison to the parent strain, revealing that the mutant acquired high 2-deoxyglucose resistance.

Example 12

Production of Inositol by Fermentation Using 2-deoxyglucose-resistant Mutant

A control strain *Candida boidinii* IP-2, and a 2-deoxyglucose-resistant mutant of the present invention *Candida boidinii* DGR 1-14 were separately precultured in a medium having the composition shown in Table 23 at 30° C. for 24 hours with shaking, and the resulting preculture was inoculated into 50 ml of medium shown in Table 23 in a 50 ml conical flask, which previously had been sterilized at 110° C. for 10 minutes, and culturing was carried out with shaking with 30 cm reciprocating span at 180 rpm for 48 hours.

TABLE 23

| | |
|---|---|
| Glucose | 50 g/L |
| $(NH_4)_2SO_4$ | 2.5 g/L |
| $KH_2PO_4$ | 1 g/L |
| $MgSO_4.7H_2O$ | 0.5 g/L |
| $CaCl_2.2H_2O$ | 0.1 g/L |
| NaCl | 0.1 g/L |
| $ZnSO_4.7H_2O$ | 0.4 g/L |
| $FeSO_4.7H_2O$ | 0.4 mg/L |
| $CuSO_4.5H_2O$ | 0.04 mg/L |
| Biotin | 0.04 mg/L |
| pH 5.5 with 1N KOH | |

After culturing, the culture medium was filtrated to eliminate the cells and remaining calcium carbonate, and an inositol concentration in the filtrate was determined by bioassay. As a result, the control strain *Candida boidinii* IP-2 extracellularly accumulated 1.5 g/L of inositol, while the 2-deoxyglucose-resistant strain of the present invention *Candida boidinii* DGR 1-14 extracellularly accumulated 3.2 g/L of inositol.

Example 13

Production of Inositol by Enzymatic Method Using 2-deoxyglucose-resistant Mutant A control strain *Candida boidinii* IP-2, and a 2-deoxyglucose-resistant mutant of the present invention *Candida boidinii* DGR 1-14 were separately precultured in a medium having the composition shown in Table 21 at 30° C. for 24 hours with shaking, and the resulting preculture was inoculated into 10 ml of media having the composition shown in Tables 24 and 25 in test tubes having 25 mm diameter, which previously had been sterilized at 115° C. for 10 minutes, and culturing was carried out at 30° C. for 24 hours with shaking.

TABLE 24

| | |
|---|---|
| Glucose | 10 g/L |
| $(NH_4)_2SO_4$ | 2.5 g/L |
| $KH_2PO_4$ | 0.5 g/L |
| $K_2HPO_4$ | 1 g/L |
| $MgSO_4.7H_2O$ | 0.5 g/L |
| $NH_4Cl$ | 4 g/L |

TABLE 25

| | |
|---|---|
| Methanol | 2% (V/V) |
| (NH$_4$)$_2$SO$_4$ | 2.5 g/L |
| KH$_2$PO$_4$ | 0.5 g/L |
| K$_2$HPO$_4$ | 1 g/L |
| MgSO$_4$.7H$_2$O | 0.5 g/L |
| NH$_4$Cl | 4 g/L |

The cultured cells were separated from the medium by centrifugation, and the separated yeast cells were dispersed in distilled water to a concentration of cells of 80 g/L (dry weight equivalent), and the suspension was allowed to stand at 37° C. for 45 minutes. After that, 4 mol/L D-sorbitol aqueous solution was added to the cell suspension to make final D-sorbitol concentration 1.5 mol/L, and the whole was allowed to stand at 37° C. for 10 minutes.

The treated cells were suspended in media having the composition shown in Tables 26 and 27, and the suspension was incubated at 30° C. for 20 hours with shaking.

TABLE 26

| | |
|---|---|
| 100 mM | Tris-HCl buffer (pH 7.5) |
| 14 mM | NH$_4$Cl |
| 2.7 mM | MgCl$_2$.6H$_2$O |
| 0.8 mM | Nicotinamide adenine dinucleotide (NAD) |
| 5 mM | Glucose-6-phosphate (substrate) |

TABLE 27

| | |
|---|---|
| 100 mm | Tris-HCl buffer (pH 7.5) |
| 14 mM | NH$_4$Cl |
| 2.7 mM | MgCl$_2$.6H$_2$O |
| 0.8 mM | NAD |
| 5 mM | Glucose (substrate) |
| 2.5 mM | Adenosine-triphosphate |

After the reaction, the reaction medium was filtrated to eliminate the cells, and an inositol concentration in the filtrate was quantitated by bioassay. Result is shown in Tables 28 and 29.

TABLE 28

Substrate: glucose-6-phosphate

| | Inositol concentration (g/L) | |
|---|---|---|
| Strains | Methanol culture | Glucose culture |
| Candida boidinii IP-2 (control) | 0.3 | 0.5 |
| Candida boidinii DGR 1-14 (present invention) | 0.6 | 1.0 |

TABLE 29

Substrate: Glucose

| | Inositol concentration (g/L) | |
|---|---|---|
| Strains | Methanol culture | Glucose culture |
| Candida boidinii IP-2 (control) | 0.3 | 0.5 |
| Candida boidinii DGR 1-14 (present invention) | 0.6 | 1.0 |

Example 14

Purification and Crystallization of Inositol

A supernatant of one liter of the culture obtained in Example 12 was passed through cation exchange resin Diaion SK1B, and flow-through fractions were pooled. The collected flow-through fraction was passed through anion exchange resin Diaion PA316, and flow-through fractions were pooled. This fraction was concentrated to crystallize inositol. In this way, 2.1 g of crystals of inositol in 97% purity was obtained.

Example 15

Isolation of D-cycloserine-resistant Mutant

Cells of *Candida boidinii* IP-2 were treated with 300 μg/ml of N-methyl-N'-nitro-N-nitrosoguanidine at 30° C. and at pH 6.0 for 10 minutes, and the mutagen-treated cells were appropriately diluted, and coated on a plate medium having the composition shown in Table 30 to which 15 g/L of agar and 200 mg/L of D-cycloserine were added. The plate was incubated at 30° C. for 4 days, and colonies of mutated *Candida boidinii* IP-2 formed on the plate were isolated and purified. In this way *Candida boidinii* DCSR 0.2-59 and *Candida boidinii* DCSR 0.3-11 were obtained.

TABLE 30

| | |
|---|---|
| Glycerol | 10 g/L |
| (NH$_4$)$_2$SO$_4$ | 5 g/L |
| KH$_2$PO$_4$ | 1 g/L |
| MgSO$_4$.7H$_2$O | 0.5 g/L |
| CaCl$_2$.2H$_2$O | 0.1 g/L |
| NaCl | 0.1 g/L |
| ZnSO$_4$.7H$_2$O | 0.4 mg/L |
| FeSO$_4$.7H$_2$O | 0.4 mg/L |
| CuSO$_4$.5H$_2$O | 0.04 mg/L |
| Biotin | 0.04 mg/L |
| pH 5.5 with 1N KOH | | pH 5.5 with 1N KOH

Example 16

Resistance Level of D-cycloserine-resistant Mutant

A control strain *Candida boidinii* IP-2, as well as D-cycloserine-resistant mutants *Candida boidinii* DCSR 0.2-59 and DCSR 0.3-11 were separately cultured in a medium having the composition shown in Table 31, and the grown cells were collected and washed with physiological saline.

TABLE 31

| | |
|---|---|
| Glucose | 20 g/L |
| Yeast extract | 2 g/L |
| MgSO$_4$.7H$_2$O | 0.5 g/L |
| Polypeptone | 5 g/L |
| K$_2$HPO$_4$ | 1 g/L |

The cell suspension thus prepared was inoculated into 5 ml of media having the composition shown in Table 30 and containing 0, 100, 200, 300, and 400 mg/L of D-cycloserine respectively. After culturing for 72 hours, the growth of cells was measured. The result is shown in Table 32.

TABLE 32

| | Relative growth (%) Concentration of D-cycloserine added (mg/L) | | | | |
|---|---|---|---|---|---|
| Strain | 0 | 100 | 200 | 300 | 400 |
| IP-2 (control) | 100 | 2 | 0 | 0 | 0 |
| DCSR 0.2-59 (present invention) | 100 | 96 | 94 | 31 | 2 |
| DCSR 0.3-11 (present invention) | 100 | 98 | 97 | 92 | 4 |

As seen from the above result, the growth of the D-cycloserine-resistant mutant of the present invention is not inhibited by high concentration of D-cycloserine in comparison with the parent strain, revealing that the mutant acquired high D-cycloserine resistance.

Example 17

Production of Inositol by Fermentation Using D-cycloserine-resistant Mutants

A control strain *Candida boidinii* IP-2, as well as D-cycloserine-resistant mutants of the present invention *Candida boidinii* DCSR 0.2-59 and DCSR 0.3-11 were separately precultured in a medium having the composition shown in Table 33 at 30° C. for 24 hours with shaking, and the resulting preculture was inoculated into 50 ml of medium shown in Table 33 in a 50 ml conical flask, which previously had been sterilized at 110° C. for 10 minutes, and culturing was carried out with shaking with 30 cm reciprocating span at 180 rpm for 48 hours.

TABLE 33

| Glucose | 50 g/L |
|---|---|
| $(NH_4)_2SO_4$ | 2.5 g/L |
| $KH_2PO_4$ | 1 g/L |
| $MgSO_4.7H_2O$ | 0.5 g/L |
| $CaCl_2.2H_2O$ | 0.1 g/L |
| NaCl | 0.1 g/L |
| $ZnSO_4.7H_2O$ | 0.4 g/L |
| $FeSO_4.7H_2O$ | 0.4 mg/L |
| $CuSO_4.5H_2O$ | 0.04 mg/L |
| Biotin | 0.04 mg/L |
| pH 5.5 with 1N KOH | | pH 5.5 with 1N KOH

After culturing, the culture medium was filtrated to eliminate the cells and remaining calcium carbonate, and an inositol concentration in the filtrate was determined by bioassay. As a result, the control strain *Candida boidinii* IP-2 extracellularly accumulated 1.5 g/L of inositol, while the D-cycloserine-resistant strains of the present invention *Candida boidinii* DCSR 0.2-59 and DCSR 0.3-11 extracellularly accumulated 3.6 g/L and 4.3 g/L of inositol respectively.

Example 18

Production of Inositol by Enzymatic Method Using D-cycloserine-resistant Mutants A control strain *Candida boidinii* IP-2, as well as a D-cycloserine-resistant mutants of the present invention *Candida boidinii* DCSR 0.2-59 and DCSR 0.3-11 were separately precultured in a medium having the composition shown in Table 11 at 30° C. for 24 hours with shaking, and the resulting preculture was inoculated into 10 ml of media having the compositions shown in Tables 34 and 35 in test tubes having 25 mm diameter, which previously had been sterilized at 115° C. for 10 minutes, and culturing was carried out at 30° C. for 24 hours with shaking.

TABLE 34

| Glucose | 10 g/L |
|---|---|
| $(KH_4)_2SO_4$ | 2.5 g/L |
| $KH_2PO_4$ | 0.5 g/L |
| $K_2HPO_4$ | 1 g/L |
| $MgSO_4.7H_2O$ | 0.5 g/L |
| $NH_4Cl$ | 4 g/L |

TABLE 35

| Methanol | 2% (V/V) |
|---|---|
| $(NH_4)_2SO_4$ | 2.5 g/L |
| $KH_2PO_4$ | 0.5 g/L |
| $K_2HPO_4$ | 1 g/L |
| $MgSO_4.7H_2O$ | 0.5 g/L |
| $NH_4Cl$ | 4 g/L |

The cultured cells were separated from the medium by centrifugation and the separated yeast cells were dispersed in distilled water to a concentration of cells of 80 g/L (dry weight equivalent), and the suspension was allowed to stand at 37° C. for 45 minutes. After that, 4 mol/L D-sorbitol aqueous solution was added to the cell suspension to make the final D-sorbitol concentration 1.5 mol/L, and the whole was allowed to stand at 37° C. for 10 minutes.

The treated cells were suspended in media having the composition shown in Tables 36 and 37, and the suspension was incubated at 30° C. for 20 hours with shaking.

TABLE 36

| 100 mM | Tris-HCl buffer (pH 7.5) |
|---|---|
| 14 mM | $NH_4Cl$ |
| 2.7 mM | $MgCl_2.6H_2O$ |
| 0.8 mM | Nicotinamide adenine dinucleotide (NAD) |
| 5 mM | Glucose-6-phosphate (substrate) |

TABLE 37

| 100 mM | Tris-HCl buffer (pH 7.5) |
|---|---|
| 14 mM | $NH_4Cl$ |
| 2.7 mM | $MgCl_2.6H_2O$ |
| 0.8 mM | NAD |
| 5 mM | Glucose (substrate) |
| 2.5 mM | Adenosine-triphosphate |

After the reaction, the reaction medium was filtrated to eliminate the cells, and an inositol concentration in the filtrate was quantitated by bioassay. Result is shown in Tables 38 and 39.

TABLE 38

| | Substrate: glucose-6-phosphate | |
|---|---|---|
| | Inositol concentration (g/L) | |
| Strains | Methanol culture | Glucose culture |
| *Candida boidinii* IP-2 (control) | 0.3 | 0.5 |
| *Candida boidinii* DCSR 0.2-59 (present invention) | 0.8 | 1.2 |

TABLE 38-continued

Substrate: glucose-6-phosphate

| Strains | Inositol concentration (g/L) | |
|---|---|---|
| | Methanol culture | Glucose culture |
| Candida boidinii DCSR 0.3-11 (present invention) | 1.0 | 1.6 |

TABLE 39

Substrate: glucose

| Strains | Inositol concentration (g/L) | |
|---|---|---|
| | Methanol culture | Glucose culture |
| Candida boidinii IP-2 (control) | 0.3 | 0.5 |
| Candida boidinii DCSR 0.2-59 (present invention) | 0.7 | 1.2 |
| Candida boidinii DCSR 0.3-11 (present invention) | 1.0 | 1.6 |

As seen from the above, the cerulenine-resistant mutant of the present invention shows remarkably enhanced productivity of inositol in comparison with the parent strain.

Example 19

Purification and Crystallization of Inositol

Two supernatants of one liter of the cultures obtained in Example 17 were passed through cation exchange resin Diaion SK1B, and flow-through fractions were pooled. The collected two flow-through fractions were passed through anion exchange resin Diaion PA316, and flow-through fractions were pooled. These two fractions were concentrated to crystallize inositol. In this way, 2.2 g and 3.0 g of crystals of inositol in 97% purity were obtained from the supernatants of DCSR 0.2-59 and DCSR 0.3-11 respectively.

We claim:

1. A process for the production of inositol comprising the steps of:
   (1) culturing a microorganism capable of extracellularly secreting inositol in an amount of more than 1.5 g/L and belonging to the species *Candida boidinii* in a medium so as to extracellularly accumulate inositol in the medium; and optionally,
   (2) recovering inositol from the culture.

2. A process according to claim 1, wherein the *Candida boidinii* is *Candida boidinii* IP-2.

3. A process for the production of inositol comprising the steps of:
   (1) culturing a microorganism capable of extracellularly secreting inositol in an amount of more than 0.3 g/L and belonging to the species *Candida boidinii* in a medium to obtain the cultured cells containing enzymes necessary for the biosynthesis of inositol;
   (2) incubating the enzymes with a precursor for the biosynthesis of inositol in a reaction medium so as to convert the precursor to inositol resulting in accumulation of inositol in the reaction medium; and optionally
   (3) recovering inositol from the reaction medium.

4. A process according to claim 3, wherein the *Candida boidinii* is *Candida boidinii* IP-2.

5. A process according to claim 3, wherein the precursor is glucose-6-phosphate or glucose.

6. A process for the production of inositol comprising the steps of:
   (1) culturing a microorganism capable of extracellularly secreting inositol in an amount of more than 2.7 g/L, belonging to the species *Candida boidinii* and resistant to an antibiotic in a medium so as to extracellularly accumulate inositol in the medium; and optionally
   (2) recovering inositol from the culture.

7. A process according to claim 6, wherein the *Candida boidinii* is *Candida boidinii* CER 176, DCSR 0.2-59 or DCSR 0.3-11.

8. A process according to claim 6, wherein the antibiotic is cerulenine, D-cycloserine or Brefeldin A.

9. A process for the production of inositol comprising the steps of:
   (1) culturing a microorganism capable of extracellularly secreting inositol in an amount of more than 0.6 g/L, belonging to the species *Candida boidinii* and resistant to antibiotic in a medium to obtain the cultured cells containing enzymes necessary for the biosynthesis of inositol;
   (2) incubating the enzymes with a precursor for the biosynthesis of inositol in a reaction medium so as to convert the precursor to inositol resulting in accumulation of inositol in the reaction medium; and optionally
   (3) recovering inositol from the reaction medium.

10. A process according to claim 9, wherein the *Candid boidinii* is *Candida boidinii* CER 176, DCSR 0.2-59 or DCSR 0.3-11.

11. A process according to claim 9, wherein the precusor is glucose-6-phosphate or glucose.

12. A process according to claim 9, wherein the antibiotic is cerulenine, D-cycloserine or Brefeldin A.

13. A process for the production of inositol comprising the steps of:
   (1) culturing a microorganism capable of extracellularly secreting inositol in an amount of more than 3.2 g/L, belonging to the species *Candida boidinii* and resistant to glucose metabolism antagonist in a medium so as to extracellularly accumulate inositol in the medium; and optionally
   (2) recovering inositol from the culture.

14. A process according to claim 13, wherein the *Candida boidinii* is *Candida boidinii* DGR 1-14.

15. A process according to claim 13, wherein the glucose metabolism antagonist is 2-deoxyglucose, 1-thioglucose or 5-thioglucose.

16. A process for the production of inositol comprising the steps of:
   (1) culturing a microorganism capable of extracellularly secreting inositol in an amount of more than 0.6 g/L, belonging to the species *Candida boidinii* and resistant to a glucose metabolism antagonist in a medium to obtain the cultured cells containing enzymes necessary for the biosynthesis of inositol;
   (2) incubating the enzymes with a precursor for the biosynthesis of inositol in a reaction medium so as to convert the precursor to inositol resulting in accumu lation of inositol in the reaction medium; and optionally (3) recovering inositol from the reaction medium.

17. A process according to claim 16, wherein the *Candida boidinii* is *Candida boidinii* DGR 1-14.

18. A process according to claim 16, wherein the precursor is glucose-6-phosphate or glucose.

19. A process according to claim 16, wherein the glucose metabolism antagonist is 2-deoxyglucose, 1-thioglucose or 5-thioglucose.

* * * * *